United States Patent
Pratt et al.

(10) Patent No.: US 10,786,608 B2
(45) Date of Patent: Sep. 29, 2020

(54) DYNAMIC NEGATIVE-PRESSURE THERAPY WITH INSTILLATION

(71) Applicant: KCI Licensing, Inc., San Antonio, TX (US)

(72) Inventors: Benjamin Andrew Pratt, Poole (GB); James Killingworth Seddon, Ferndown (GB)

(73) Assignee: KCI Licensing, Inc., San Antonio, TX (US)

( * ) Notice: Subject to any disclaimer, the term of this patent is extended or adjusted under 35 U.S.C. 154(b) by 874 days.

(21) Appl. No.: 15/510,185

(22) PCT Filed: Sep. 10, 2015

(86) PCT No.: PCT/US2015/049476
§ 371 (c)(1),
(2) Date: Mar. 9, 2017

(87) PCT Pub. No.: WO2016/040671
PCT Pub. Date: Mar. 17, 2016

(65) Prior Publication Data
US 2017/0246363 A1     Aug. 31, 2017

Related U.S. Application Data

(60) Provisional application No. 62/048,615, filed on Sep. 10, 2014.

(51) Int. Cl.
*A61M 1/00* (2006.01)
*A61M 39/10* (2006.01)
(Continued)

(52) U.S. Cl.
CPC ..... *A61M 1/0084* (2013.01); *A61F 13/00017* (2013.01); *A61F 13/00042* (2013.01);
(Continued)

(58) Field of Classification Search
CPC ........ A61M 1/00; A61M 39/10; A61M 39/24; A61F 13/00
See application file for complete search history.

(56) References Cited

U.S. PATENT DOCUMENTS 1,355,846 A   10/1920   Rannells
2,547,758 A   4/1951    Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Nicholas J. Weiss
*Assistant Examiner* — Ilya Y Treyger

(57) ABSTRACT

Apparatuses, systems, and methods for instilling a solution to a tissue site are disclosed. In some embodiments, an instillation regulator may be fluidly coupled to a solution source and to a dressing, and the instillation regulator may draw a solution from the solution source during a negative-pressure interval may instill the solution to the dressing during a venting interval.

26 Claims, 15 Drawing Sheets

(51) Int. Cl.
  *A61M 39/24* (2006.01)
  *A61F 13/00* (2006.01)
(52) U.S. Cl.
  CPC ..... *A61F 13/00068* (2013.01); *A61M 1/0088* (2013.01); *A61M 1/0092* (2014.02); *A61M 39/105* (2013.01); *A61M 39/24* (2013.01); *A61M 2205/3331* (2013.01); *A61M 2205/7536* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,901,629 A | 8/1975 | Chancholle et al. |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,486,190 A | 12/1984 | Reinicke |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,946,448 A | 8/1990 | Richmond |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,744,278 B2 * | 8/2017 | Locke ................ A61M 1/0088 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040709 A1 | 2/2003 | Mason |
| 2012/0302976 A1 | 11/2012 | Locke et al. |
| 2014/0163491 A1 | 6/2014 | Schuessler et al. |
| 2014/0188061 A1 | 7/2014 | Locke et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| FR | 2203437 | * 10/1972 |

(56) References Cited

FOREIGN PATENT DOCUMENTS

| | | |
|---|---|---|
| FR | 2203437 A5 | 5/1974 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Japanese Notice of Rejection corresponding to Application No. 2017-513072, dated Aug. 6, 2019.

(56) References Cited

OTHER PUBLICATIONS

V.A.C. Ulta (TM) Ntegative Pressure Wound Therapy System Monograph, Nov. 2012.
V.a.c.ulta (TM) Quick Reference Guide, Sep. 2013.
Extended European Search Report for Corresponding Application No. 182152181, dated Apr. 17, 2019.

* cited by examiner

DYNAMIC NEGATIVE-PRESSURE THERAPY WITH INSTILLATION

RELATED APPLICATION

This present invention claims the benefit under 35 USC § 119(e), of the filing of PCT/US2015/049476, "DYNAMIC NEGATIVE-PRESSURE THERAPY WITH INSTILLATION," filed Sep. 10, 2015 and U.S. Provisional Patent Application Ser. No. 62/048,615, entitled "DYNAMIC NEGATIVE-PRESSURE THERAPY WITH INSTILLATION," filed Sep. 10, 2014, which is incorporated herein by reference for all purposes.

TECHNICAL FIELD

The invention set forth in the appended claims relates generally to tissue treatment systems and more particularly, but without limitation, to apparatuses and methods for providing negative pressure therapy with instillation of topical treatment solutions.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of a wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for instilling fluid to a tissue site in a negative-pressure therapy environment are set forth in the appended claims. Illustrative embodiments are also provided to enable a person skilled in the art to make and use the claimed subject matter. Some embodiments are illustrative of a mechanically-operated, positively-pressurized, disposable instillation system. Illustrative embodiments of an instillation regulator are also described herein, which may be used to combine instillation therapy and negative-pressure therapy. For example, some embodiments are illustrative of an instillation regulator that can draw a solution from a solution source during a negative-pressure interval and instill the solution to a dressing during a venting interval.

According to some illustrative embodiments, an instillation regulator may comprise a first chamber and a second chamber, separated by a piston. An inlet check valve may be fluidly coupled to the first chamber, a first outlet check valve may be fluidly coupled to the first chamber, and a second outlet check valve may be fluidly coupled to the second chamber. A flow limiter may also be fluidly coupled to the second chamber in some embodiments. The piston may be configured to be displaced by a pressure differential between the first chamber and the second chamber, and a spring may be operably disposed in the second chamber against the piston to bias the piston.

Additionally or alternatively, apparatuses for instilling a solution to a tissue site are described. Some illustrative embodiments may include a housing comprised of a head coupled to a body to enclose a piston disposed in a cavity. The piston may be disposed in the cavity and partition the cavity into a first chamber and a second chamber. A spring may be disposed within the second chamber between the piston and the body. The body may comprise a negative-pressure port and a vent, and the head may comprise an extension, a solution inlet port, and a solution outlet port. In some embodiments, a first outlet check can be fluidly coupled to the extension between the first chamber and the solution outlet port, and can be configured to be closed by negative pressure in the first chamber. An inlet check valve may also be fluidly coupled to the first chamber and configured to be opened by negative pressure in the first chamber in some embodiments. A second outlet check valve may be fluidly coupled to the second chamber and configured to be opened by negative pressure delivered to the negative pressure port. Additionally, some embodiments may further include a flow limiter comprising a hydrophobic filter disposed in the vent.

Yet other illustrative embodiments of an apparatus for instilling a solution may include a body and a head coupled to the body to enclose a piston disposed in a cavity. The piston may partition the cavity into a first chamber and a second chamber. A spring may be disposed within the second chamber between the piston and the body. The head may include an extension, a first fluid port, and a second fluid port. In some embodiments, a first channel may also be integrally molded in the head, and a second channel integrally may be molded in the body and fluidly coupled to the second chamber. A passage may be integrally molded along a length of the body in some embodiments, and the passage can be fluidly coupled to the first channel and to the second channel. A first outlet check can be fluidly coupled to the extension between the first chamber and the second fluid port, and the first outlet check valve can be configured to be closed by negative pressure in the first chamber. An inlet check valve may be fluidly coupled to the first chamber and configured to be opened by negative pressure in the first chamber. A second outlet check valve can be fluidly coupled to the second chamber and configured to be opened by negative pressure in the second channel.

Additionally or alternatively, illustrative embodiments of a therapy system are described for treating a tissue site with negative pressure therapy and instillation therapy. According to some embodiments, a therapy system may include a dressing, a negative-pressure source fluidly coupled to the dressing, a solution source, and an instillation regulator. The negative-pressure source may be configured to cycle between a negative-pressure interval and a venting interval. The installation regulator may be fluidly coupled to the solution source and the dressing to draw a solution from the solution source during a negative-pressure interval and to instill the solution to the dressing during a venting interval. According to more particular embodiments, the installation regulator may comprise a housing having a cavity and a piston that partitions the cavity into a first chamber and a second chamber. An inlet check valve and a first outlet check valve may be fluidly coupled to the first chamber, and a second outlet check valve may be fluidly coupled to the second chamber.

Illustrative embodiments of methods for treating a tissue site are also described. For example, in some embodiments, a method for treating a tissue site may include applying a dressing to the tissue site, coupling a negative pressure source and an installation regulator to the dressing, and coupling a solution source to the installation regulator. The negative-pressure source may be configured for dynamic or intermittent negative-pressure therapy, providing intervals of negative-pressure and venting. A therapeutic solution may be drawn from solution source to the installation regulator during a negative-pressure interval, and the solution may be instilled from the installation regulator to the dressing during a venting interval.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
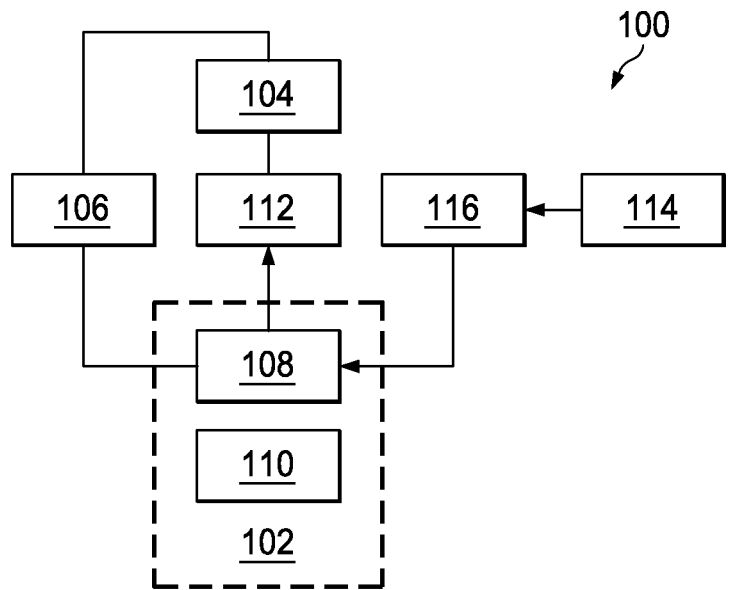
FIG. 1 is a functional block diagram of an example embodiment of a therapy system that can manage fluids in accordance with this specification.

FIG. 1 is a simplified block diagram of an example embodiment of a therapy system 100 that can provide negative-pressure therapy with instillation of topical treatment solutions in accordance with this specification. The therapy system 100 may include a dressing and a negative-pressure source. For example, a dressing 102 may be fluidly coupled to a negative-pressure source 104, as illustrated in FIG. 1. A regulator, such as a pressure regulator 106, may also be fluidly coupled to the dressing 102 and the negative-pressure source 104. A dressing may include a cover and a tissue interface. The dressing 102, for example, includes a cover 108 and a tissue interface 110. The therapy system 100 may also include an exudate container, such as a container 112, coupled to the dressing 102 and to the negative-pressure source 104.

The therapy system 100 may also include a source of instillation solution. For example, a solution source 114 may be fluidly coupled to the dressing 102, as illustrated in the example embodiment of FIG. 1. A second regulator, such as an installation regulator 116, may also be fluidly coupled to the solution source 114 and the dressing 102. In some embodiments, the installation regulator 116 may also be fluidly coupled to the negative-pressure source 104 through the dressing 102, as illustrated in the example of FIG. 1.

In general, components of the therapy system 100 may be coupled directly or indirectly. For example, the negative-pressure source 104 may be directly coupled to the pressure regulator 106 and indirectly coupled to the dressing 102 through the pressure regulator 106. In some embodiments, components may be coupled by virtue of physical proximity, being integral to a single structure, or being formed from the same piece of material. Coupling may also include mechanical, thermal, electrical, or chemical coupling (such as a chemical bond) in some contexts.

Components may also be fluidly coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other fluid conductor with one or more lumina adapted to convey fluid between two ends. Typically, a tube is an elongated, cylindrical structure with some flexibility, but the geometry and rigidity may vary. A fluid conductor may also be integrally molded into a component in some embodiments.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across a tissue site through the tissue interface 110 in the sealed therapeutic environment can induce macro-strain and micro-strain in the tissue site, as well as remove exudate and other fluid from the tissue site, which can be collected in the container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art.

In general, fluid flows toward lower pressure along a fluid path. Thus, the term "downstream" typically implies something in a fluid path relatively closer to a source of negative pressure or further away from a source of positive pressure; conversely, the term "upstream" implies something relatively further away from a source of negative pressure or closer to a source of positive pressure. Similarly, it may be convenient to describe certain features in terms of fluid "inlet" or "outlet" in such a frame of reference, and the process of reducing pressure may be described illustratively herein as "delivering," "distributing," or "generating" reduced pressure, for example. This orientation is generally presumed for purposes of describing various features and components herein.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, negative pressure may be a pressure less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with a tissue site. If a tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites. In some embodiments, the tissue interface may be provided in a spiral cut sheet. Moreover, any or all of the surfaces of the tissue interface 110 may have an uneven, coarse, or jagged profile that can induce micro-strains and stresses at a tissue site.

In some embodiments, the tissue interface 110 may be a manifold. A "manifold" in this context generally includes any substance or structure providing a plurality of pathways adapted to collect or distribute fluid across a tissue site. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate distributing fluid across a tissue site.

In some illustrative embodiments, the pathways of a manifold may be interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and fluid pathways. In some illustrative embodiments, a manifold may be a porous foam material having interconnected cells or pores adapted to distribute negative pressure across a tissue site. The foam material may be either hydrophobic or hydrophilic. The pore size of a foam material may vary according to needs of a prescribed therapy. For example, in some embodiments, the tissue interface 110 may be a foam having pore sizes in a range of 400-600 microns. The tensile strength of the tissue interface 110 may also vary according to needs of a prescribed therapy. For example, the tensile strength of a foam may be increased for instillation of topical treatment solutions. In one non-limiting example, the tissue interface 110 may be an open-cell, reticulated polyurethane foam such as GranuFoam® dressing available from Kinetic Concepts, Inc. of San Antonio, Tex.; in other embodiments the tissue interface 110 may be an open-cell, reticulated polyurethane foam such as a VeraFlo® foam, also available from Kinetic Concepts, Inc., of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or the entire cover 108. In some embodiments, for example, some or all of the cover 108 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudate and other fluid withdrawn from a tissue site. In many environments, a rigid container may be preferred or required for collecting, storing, and disposing of fluid. In other environments, fluid may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

Figure 2:
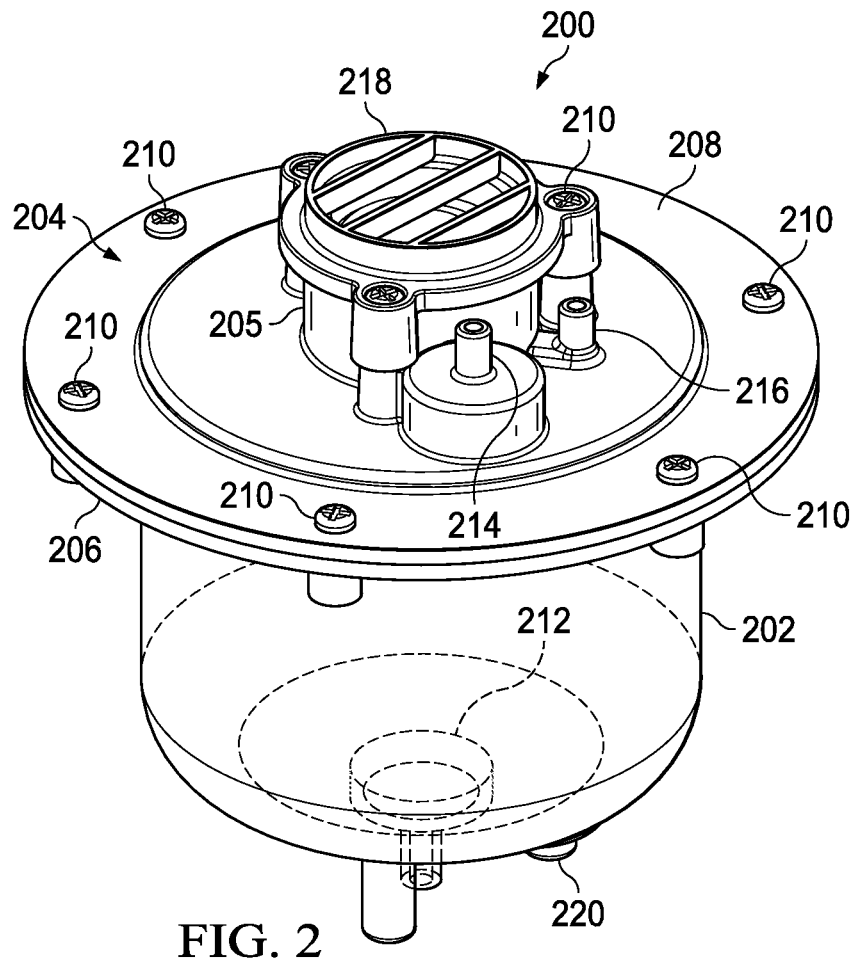
FIG. 2 is a perspective view illustrating additional details that may be associated with some example embodiments of an installation regulator in the therapy system of FIG. 1.

FIG. 2 is a perspective view of an instillation regulator 200 illustrating additional details that may be associated with some embodiments of the therapy system 100. The instillation regulator 200 may be an example embodiment of the instillation regulator 116 of FIG. 1. The instillation regulator 200 generally includes a housing, which may be formed by a body 202 and a head 204 coupled to the body 202, as shown in the example embodiment of FIG. 2. Some embodiments of the head 204 may include an extension 205. In some embodiments, the body 202 may include a flange 206, and the head 204 may include a flange 208. The body 202 may be cylindrical in some embodiments, as illustrated in the example of FIG. 2, and the head 204 may be circular with a cylindrical extension 205, also as illustrated in the example of FIG. 2. The flange 206 and the flange 208 may be coupled with fasteners 210, or may be coupled with other mechanical, thermal, electrical, or chemical couplings. The dimensions of the flange 208 may be similar to the dimensions of the flange 206 to facilitate a secure coupling.

Some embodiments of the instillation regulator 200 may have fluid ports adapted for coupling to a tube. For example, as shown in FIG. 2, the body 202 may have a negative-pressure port 212, and the head 204 may have a solution inlet port 214 and a solution outlet port 216. A retention cap 218 may also be coupled to the head 204 in some embodiments of the instillation regulator 200, and the body 202 may additionally comprise a vent 220, as shown in the example embodiment of FIG. 2.

Figure 3A:
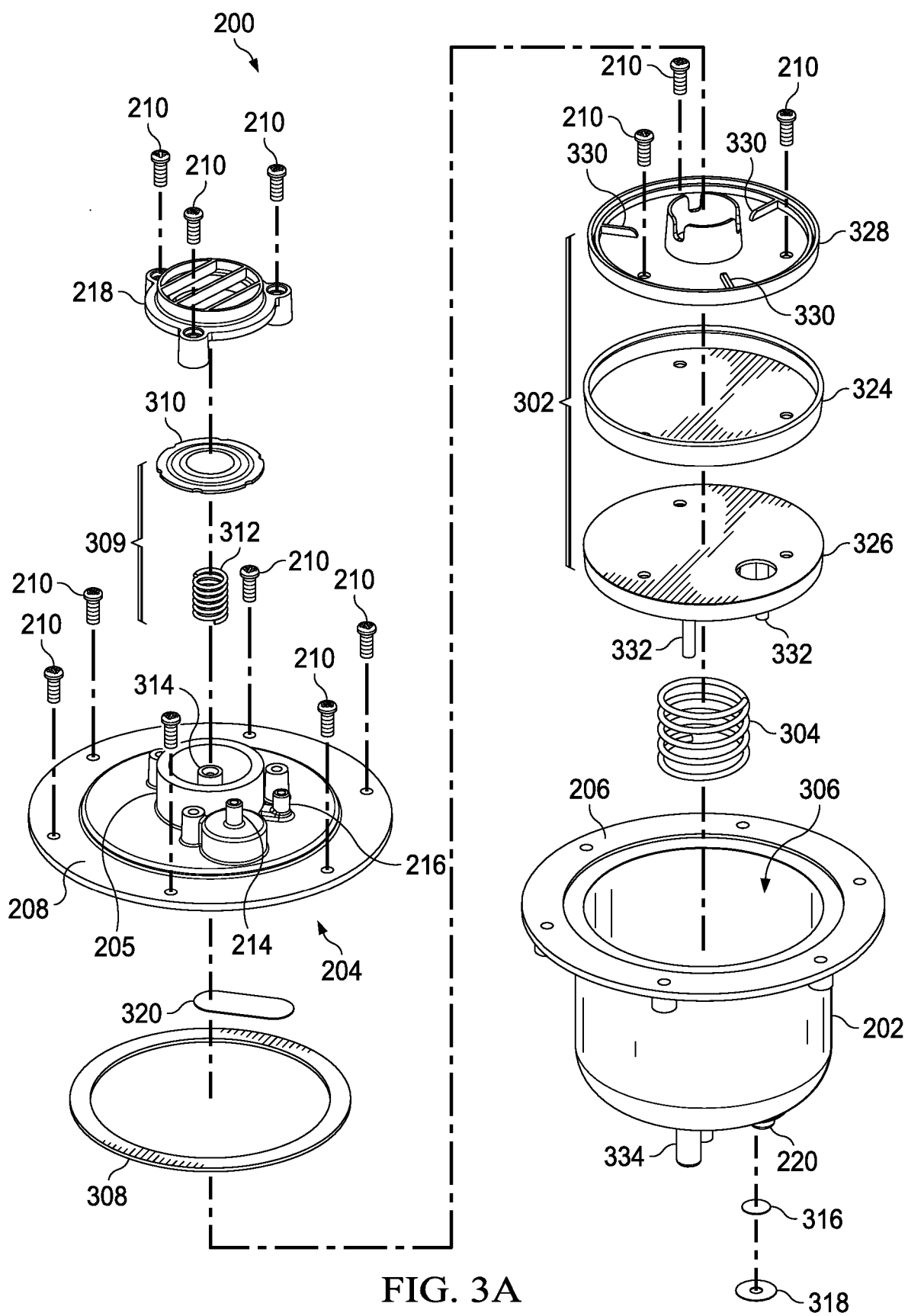
FIGS. 3A-3B are assembly views illustrating additional details that may be associated with some embodiments of the installation regulator of FIG. 2.
Figure 3B:
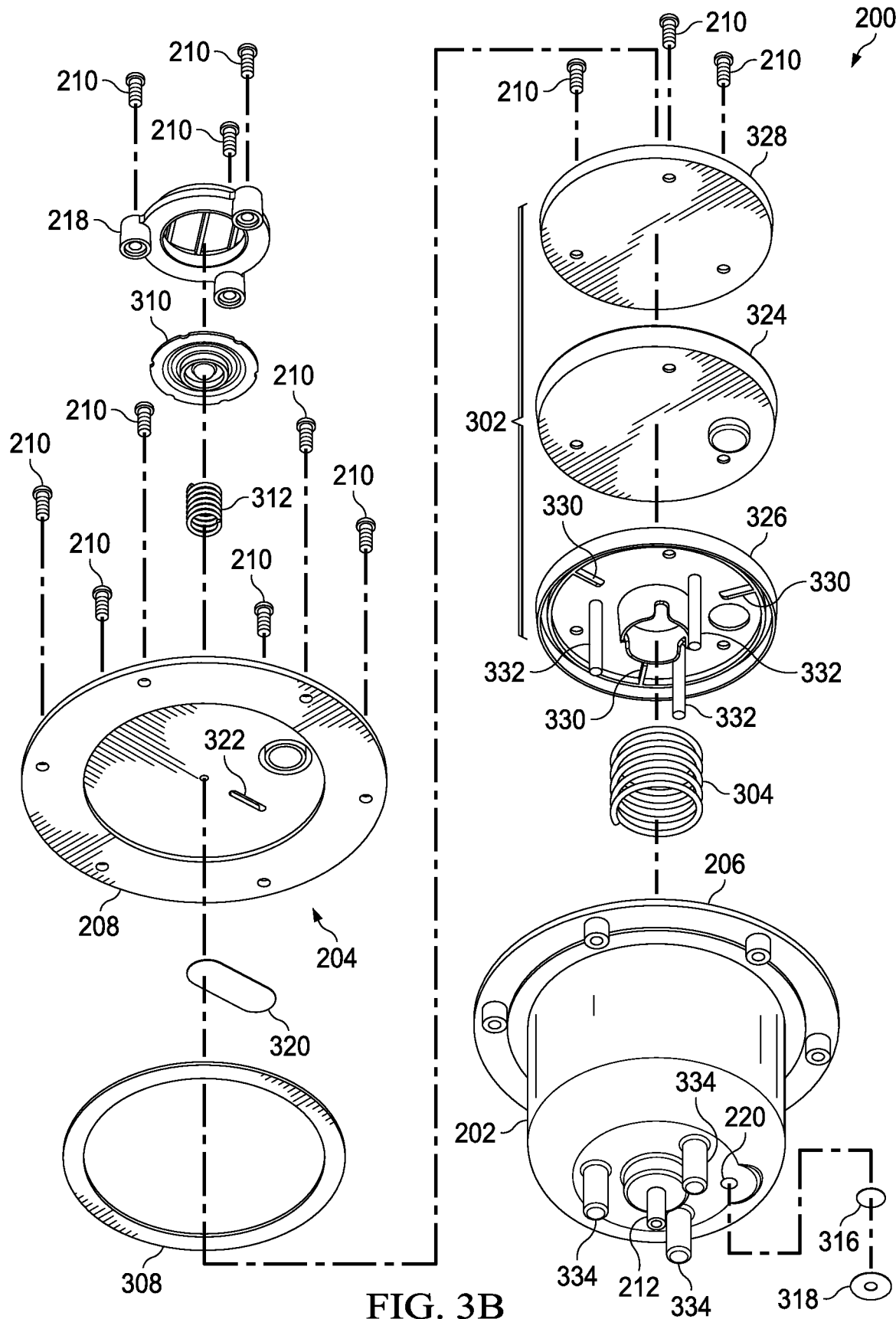

FIG. 3A and FIG. 3B are assembly views illustrating additional details that may be associated with some embodiments of an instillation regulator, such as the instillation regulator 200 of FIG. 2. Some embodiments of the instillation regulator 200 may include a piston, an elastic device, and a gasket. A piston can be a flexible or movable barrier, for example, illustrated in FIG. 3A as a piston 302. An elastic device may be a spring or rubber, for example, illustrated in FIG. 3A as a spring 304. The spring 304 may be disposed within a cavity 306 of the body 202, generally between the piston 302 and the body 202, as illustrated in the example embodiment of FIG. 3A. In some embodiments, the spring 304 may be a coil spring coaxial with the piston 302, as shown in the example of FIG. 3A. Also as shown in the example embodiment of FIG. 3A and FIG. 3B, the cavity 306 may be cylindrical, and the piston 302 may be rounded to fit within the cavity 306 of the body 202. The piston 302 may also reciprocate within the cavity 306. A gasket 308 may be disposed between the flange 206 and the flange 208.

The instillation regulator 200 may also include an outlet check valve 309 disposed between the head 204 and the retention cap 218. For example, as shown in the illustrative embodiment of FIG. 3A, some embodiments of the outlet check valve 309 may be a diaphragm valve having a diaphragm 310 and an elastic device such as a spring 312. The diaphragm 310 may be a flexible membrane or partition, such as a thin flexible disk. The spring 312 may be disposed within the extension 205 over a retention boss 314, which can restrict lateral movement of the spring 312.

Some embodiments of the instillation regulator 200 may further include a flow limiter. For example, a flow limiter may comprise a hydrophobic filter 316 and a retaining ring 318, as illustrated in FIG. 3A and FIG. 3B. The hydrophobic filter 316 is generally configured to be disposed in or otherwise engage the vent 220, and the retaining ring 318 may be disposed around or otherwise coupled to the hydrophobic filter and the vent 220 to secure the hydrophobic filter 316 to the vent 220. In some embodiments, a flow limiter may comprise an adjustable valve, such as a needle valve.

The head 204 may include a passage configured to fluidly couple the extension 205 and the solution outlet port 216. For example, the passage may be formed by a membrane 320 coupled to the head 204 to enclose a channel 322 formed in the head 204.

In some embodiments, the piston 302 may comprise a flexible seal disposed between a base and a retainer. For example, the piston 302 of FIG. 3A and FIG. 3B includes a seal 324, a seal base 326, and a seal retainer 328. The seal 324 may be an elastomer or other flexible material, for example, while the seal base 326 and the seal retainer 328 preferably provide strength and rigidity to support the seal 324. In some embodiments, the seal base 326 and the seal retainer 328 may include ribs 330 to provide further structural support. The seal base 326 may include one or more alignment pins 332, which can be configured to engage one or more alignment guides 334.

Figure 4:
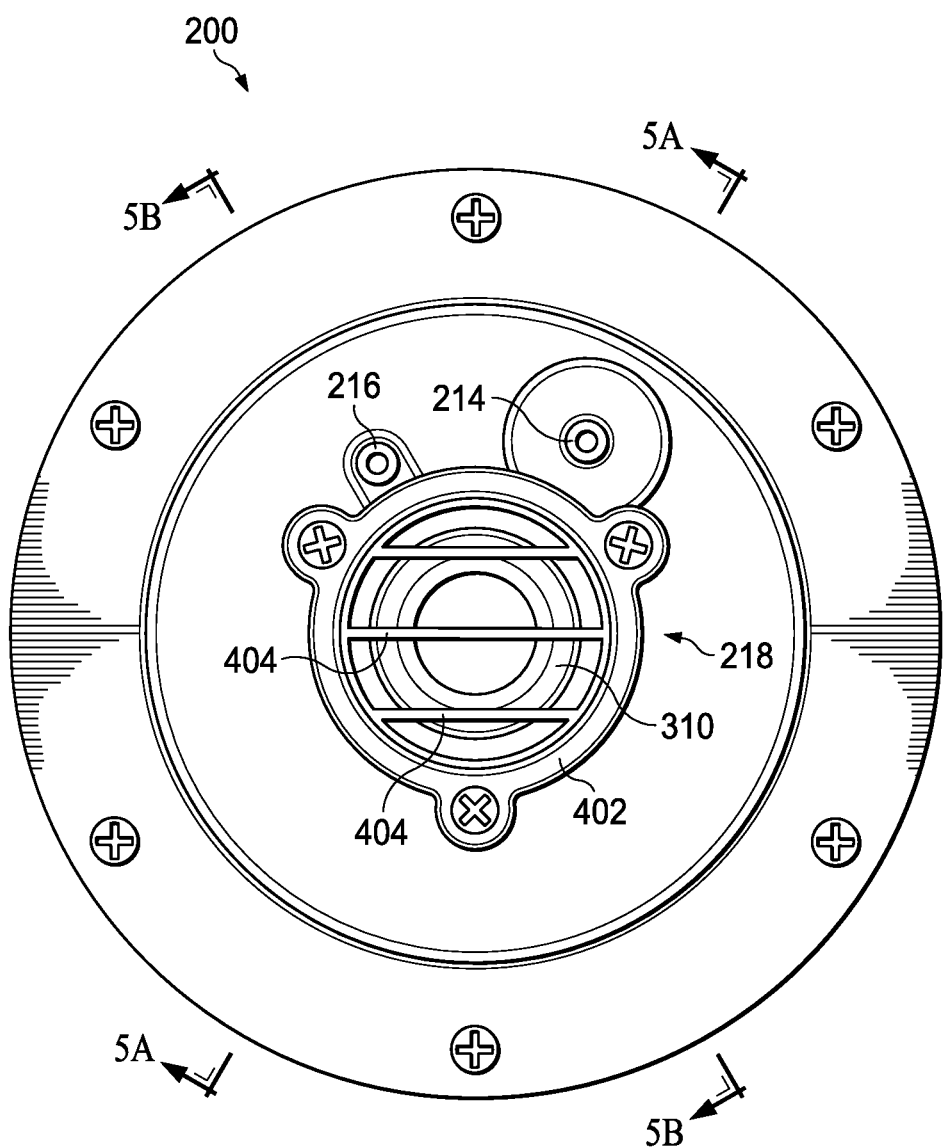
FIG. 4 is a top view illustrating additional details that may be associated with some embodiments of the installation regulator of FIG. 2.

FIG. 4 is a top view illustrating additional details that may be associated with some embodiments of an instillation regulator, such as the instillation regulator 200. As shown in the example embodiment of FIG. 4, the retention cap 218 may be vented to expose the diaphragm 310 to the ambient environment. In some embodiments, for example, the retention cap 218 may comprise a support ring 402 and cross-bars 404 coupled to the support ring 402. The cross-bars 404 are generally configured to protect the diaphragm 310 and provide a fluid path between the diaphragm 310 and the ambient environment. Additionally or alternatively, a grid, a mesh, or other suitable porous structure may be coupled to the support ring to provide similar protection and fluid communication. The solution inlet port 214 and the solution outlet port 216 may be disposed on, in, or through the head 204, adjacent to the retention cap 218 and outside the support ring 402.

Figure 5A:
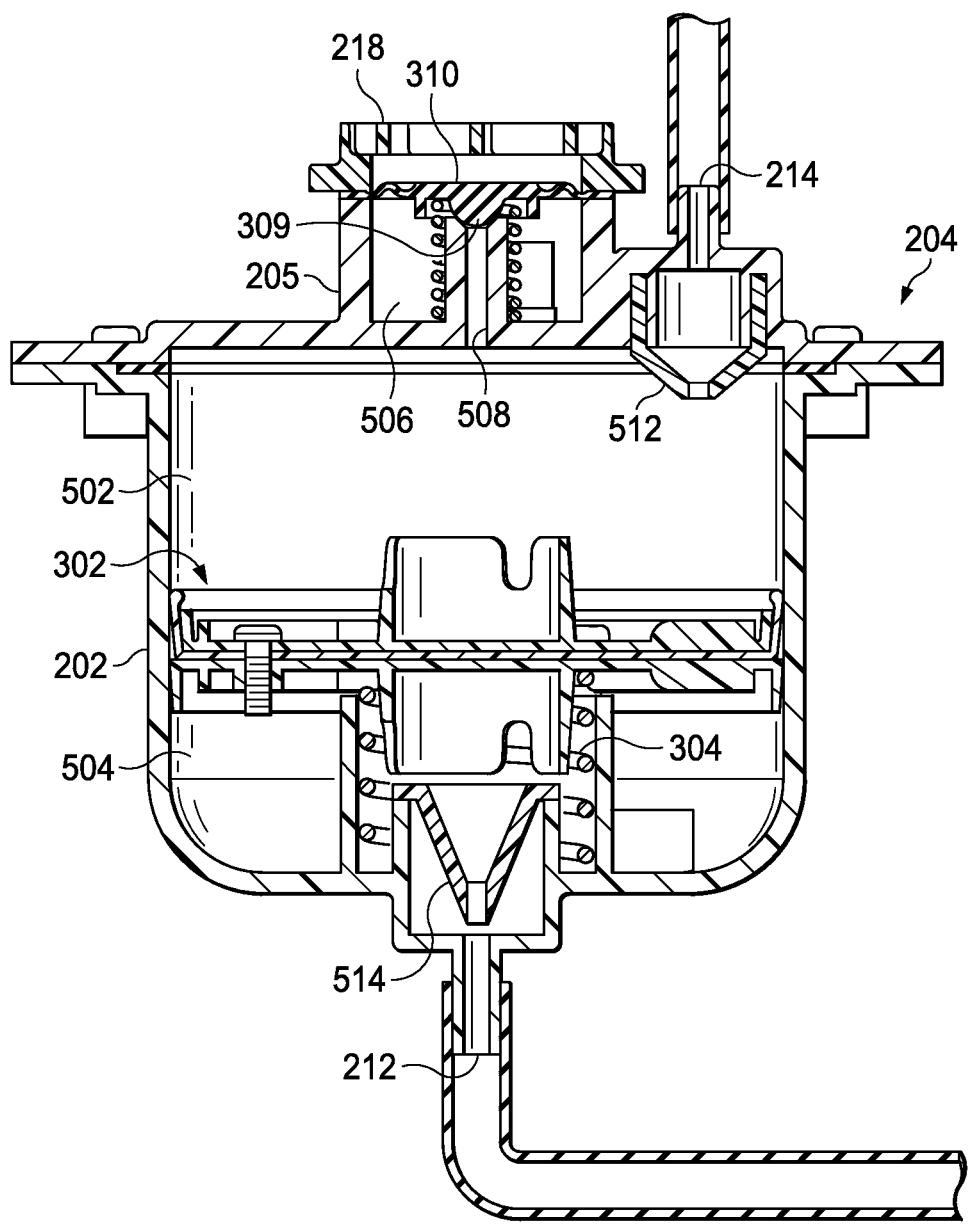
FIG. 5A is a cross-section of the installation regulator shown in FIG. 4 taken along line 5A-5A.
Figure 5B:
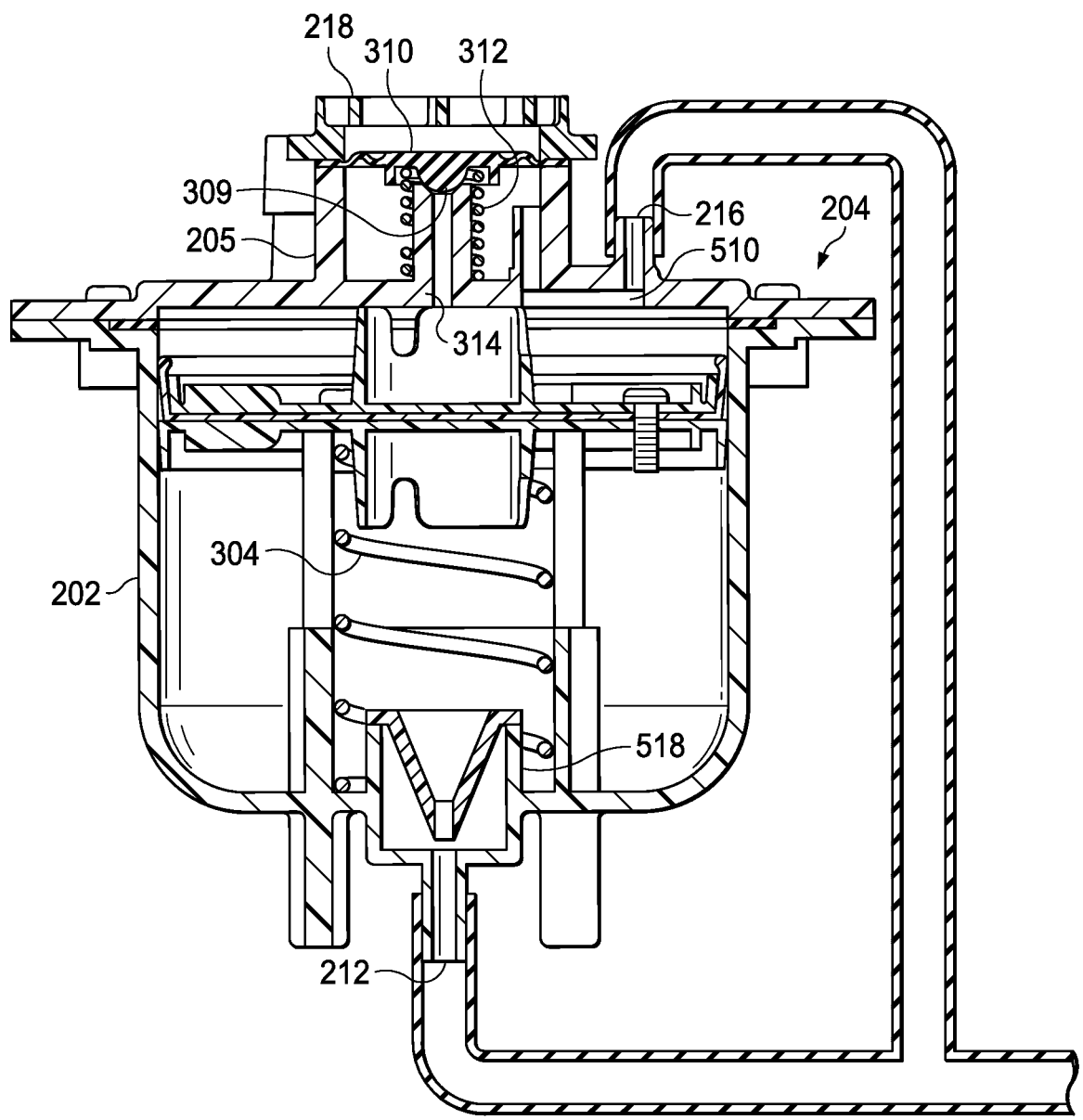
FIG. 5B is a cross-section of the installation regulator shown in FIG. 4 taken along line 5B-5B.

FIG. 5A is a sectional view of the instillation regulator 200 of FIG. 4 taken on line 5A-5A, illustrating additional details that may be associated with some embodiments of the instillation regulator 200 in a first state. FIG. 5B is a sectional view of the instillation regulator 200 of FIG. 4 taken on line 5B-5B, illustrating additional details that may be associated with some embodiments of the instillation regulator 200 in a second state. Assembled as shown in the example embodiment of FIG. 5A, the head 204 can be coupled to the body 202 to enclose the piston 302 and fluidly isolate the cavity 306 from the ambient environment. The piston 302 may partition or separate the cavity 306 into a first chamber 502 and a second chamber 504. Moreover, the piston 302 may engage the body 202 to provide a seal between the first chamber 502 and the second chamber 504. For example, as shown in the example embodiment of FIG. 5A and FIG. 5B, the seal 324 may press against a side wall of the body 202 to fluidly isolate the first chamber 502 from the second chamber 504.

The diaphragm 310 may be coupled to the extension 205 to form a third chamber 506, generally defined by a portion of the head 204, the extension 205, and the diaphragm 310. The spring 312 may be disposed in the third chamber 506 between the diaphragm 310 and the head 204. For example, the spring 312 may be disposed around the retention boss 314, as shown in the installation regulator 200 of FIG. 5A and FIG. 5B. In some embodiments, a peripheral edge of the diaphragm 310 may be supported by the extension 205, and an interior portion of the diaphragm 310 may engage the spring 312. The retention cap 218 may be coupled to the head 204 to secure the peripheral edge of the diaphragm 310 between the retention cap 218 and the extension 205. A passage 508 through the retention boss 314 can fluidly couple the first chamber 502 and the third chamber 506 through the diaphragm valve 309. A passage 510 in the head 204 may also fluidly couple the third chamber 506 to the solution outlet port 216. The passage 508 and the passage 510 can provide a fluid path between the first chamber 502 and the solution outlet port 216 through the outlet check valve 309, which may be configured to be closed by negative pressure in the first chamber 502.

Some embodiments of the regulator 200 may also include an inlet check valve 512 and an outlet check valve 514. The inlet check valve 512 may be fluidly coupled to the first chamber 502 and configured to be opened by negative pressure in the first chamber 502. The outlet check valve 514 may be fluidly coupled to the second chamber 504 and configured to be opened by negative pressure delivered to the negative-pressure port 212 or by an increase in pressure in the second chamber 504. For example, the inlet check valve 512 may be disposed between the solution inlet port 214 and the first chamber 502, and the outlet check valve 514 may be disposed between the negative-pressure port 212 and the second chamber 504.

The spring 304 may be disposed in the second chamber 504 against the piston 302 and the body 202 to bias the piston. For example, as shown in the illustrative embodiment of FIG. 5A and FIG. 5B, the piston spring 516 may have a first end disposed around a retention boss 518 to restrict lateral movement, and may have a second end engaged to the piston 302. In this example configuration, the spring 304 may bias the piston toward the head 204.

Figure 6:
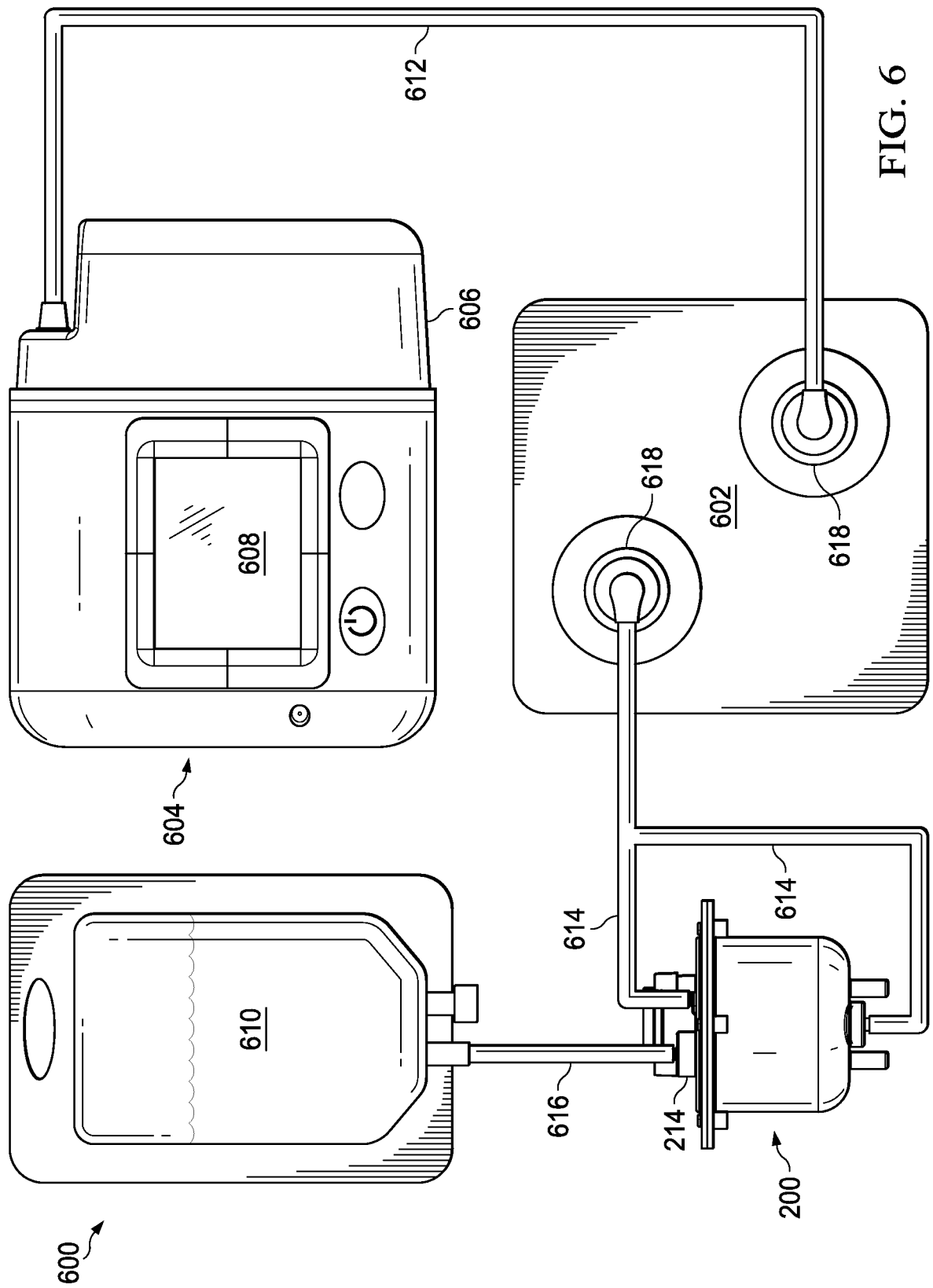
FIG. 6 is a schematic diagram of an example embodiment of the therapy system of FIG. 1.

FIG. 6 is a schematic diagram of a therapy system 600, which may be an illustrative embodiment of the therapy system 100 having an embodiment of the instillation regulator 200. The therapy system 600 may include a dressing 602 and a negative-pressure therapy unit 604. The dressing 602 may be an example embodiment of the dressing 102 of FIG. 1. The negative-pressure therapy unit 604 may comprise an internal negative-pressure source (not visible in FIG. 6) and an exudate container 606. In general, the exudate container 606 is fluidly coupled to the internal negative-pressure source when coupled to the negative-pressure therapy unit 604, but may be detachable from the negative-pressure therapy unit 604. In some embodiments, the dressing 602 may be fluidly coupled to internal negative-pressure source through the exudate container 606. In some embodiments, the negative-pressure therapy unit 604 may also include a user interface 608.

The therapy system 600 may also include an installation solution source, such as a solution bag 610, fluidly coupled to the dressing 602 as illustrated in the example embodiment of FIG. 6. The solution bag 610 may be an illustrative embodiment of the solution source 114 of FIG. 1. The solution bag 610 and the dressing 602 may be fluidly coupled to the installation regulator 200. As shown in the example embodiment of FIG. 6, the dressing 602 and the exudate container 606 can provide a fluid path between the installation regulator 200 and the negative-pressure source.

A tube 612 can fluidly couple the dressing 602 to the exudate container 606, and tubes 614 can fluidly couple the dressing 602 to the installation regulator 200. A tube 616 may also fluidly couple the solution bag 610 to the installation regulator 200. In some embodiments, elbow connectors 618 may be used to facilitate coupling the dressing 602 to the tube 612 and the tubes 614, as shown in FIG. 6.

In operation, therapy system 600 may provide intermittent or dynamic negative pressure, having negative-pressure intervals during which negative pressure is applied to the dressing 602 and venting intervals during which no negative-pressure is applied to the dressing 602. The installation regulator 200 may regulate installation during these intervals. For example, in some embodiments the installation regulator 200 may be primed during the negative-pressure intervals, and the installation regulator 200 may instill a solution from the solution bag 610 to the dressing 602 during venting intervals.

For example, the negative-pressure therapy unit 604 can remove air from the second chamber 504 during a negative-pressure interval, which can develop a pressure differential across the piston 302. This pressure differential can have the effect of moving the piston 302, expanding the first chamber 502, and compressing the second chamber 504. If the first chamber 502 expands, pressure in the first chamber 502 can decrease. Negative pressure in the first chamber 502 can then have the effect of actively drawing installation solution into the first chamber 502 from the solution bag 610 through the tube 616 and the solution inlet port 214. The distance that the piston 302 travels can determine a dosage volume of installation solution. The first chamber 502 may be lined with a suitable material to prevent contamination from mechanical components or lubricants. For example, the first chamber 502 may be lined with a film bag, an elastomeric bag, or a compressible bellows.

Expansion of the first chamber 502 may also have the effect of decreasing pressure in the third chamber 506, as pressure between the first chamber 502 and the third chamber 506 may be equalized through the passage 508. Decreased pressure in the third chamber 506 may have the effect of closing the outlet check valve 309, which can prevent installation of solution to the dressing 602 during a negative-pressure interval.

During a venting interval, the dressing 602 may vent to atmospheric pressure of the ambient environment, which can have the effect of increasing pressure in the second chamber 504. The vent 220 may also provide fluid communication between the second chamber 504 and the ambient environment, which can also have the effect increasing pressure in the second chamber 504. Increased pressure in the second chamber 504 during a venting interval can have the effect of moving the piston 302 to compress the first chamber 502 and expand the second chamber 504. If the first chamber 502 is compressed, pressure in the first chamber 502 can increase. Increased pressure can move solution out of the first chamber 502 through the solution outlet port 216, instilling the solution into the dressing 602 through the tube 614. The inlet check valve 512 can prevent back-flow through the solution inlet port 214 during installation, and the outlet check valve 514 can prevent solution from moving into the second chamber 504 through the negative-pressure port 212 during installation. A flow limiter such as the hydrophobic filter 316 can control the rate of venting between the second chamber 504 and the ambient environment through the vent 220, which can also determine the rate at which the piston 302 moves and the rate at which solution can be instilled from the chamber 502. For example, the surface area of the hydrophobic filter 316 can determine the vent rate and can be calibrated to provide a prescribed installation rate.

Figure 7:
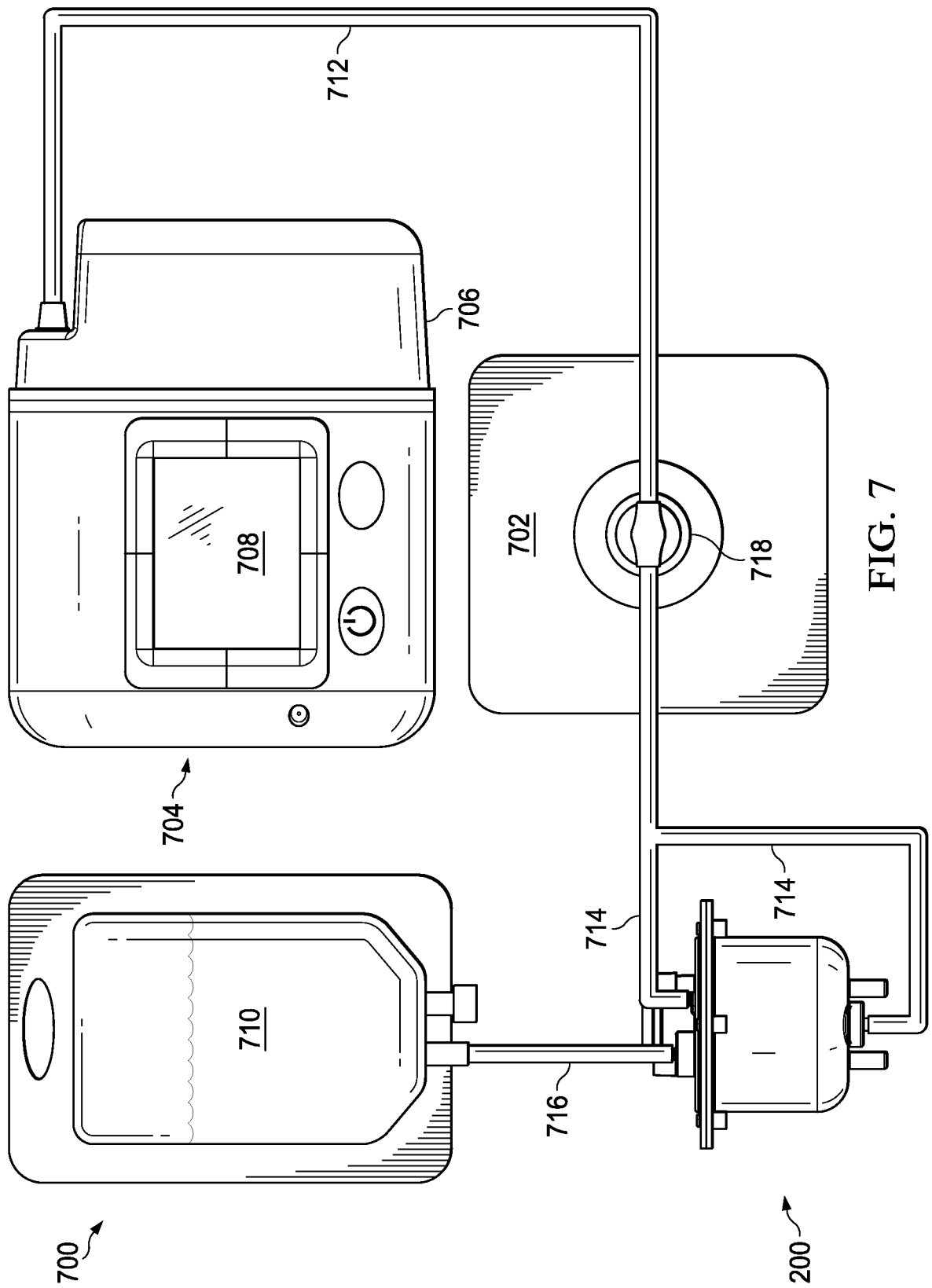
FIG. 7 is a schematic diagram of an example embodiment of the therapy system of FIG. 1.

FIG. 7 is a schematic diagram of a therapy system 700, which may be an alternative illustrative embodiment of the therapy system 100 having an embodiment of the installation regulator 200. The therapy system 700 may include a dressing 702 and a negative-pressure treatment unit 704, analogous to the dressing 602 and the negative-pressure treatment unit 604 of therapy system 600. In the embodiment of FIG. 7, tubes 712 and 714 may be fluidly coupled to the dressing 702 using a connection interface 718. In this example embodiment, connection interface 718 may be a multi-port elbow connector configured to communicate negative pressure from the tube 712, as well as conduct the passage of installation fluid delivered through tube 714 to the dressing 702.

Figure 8:
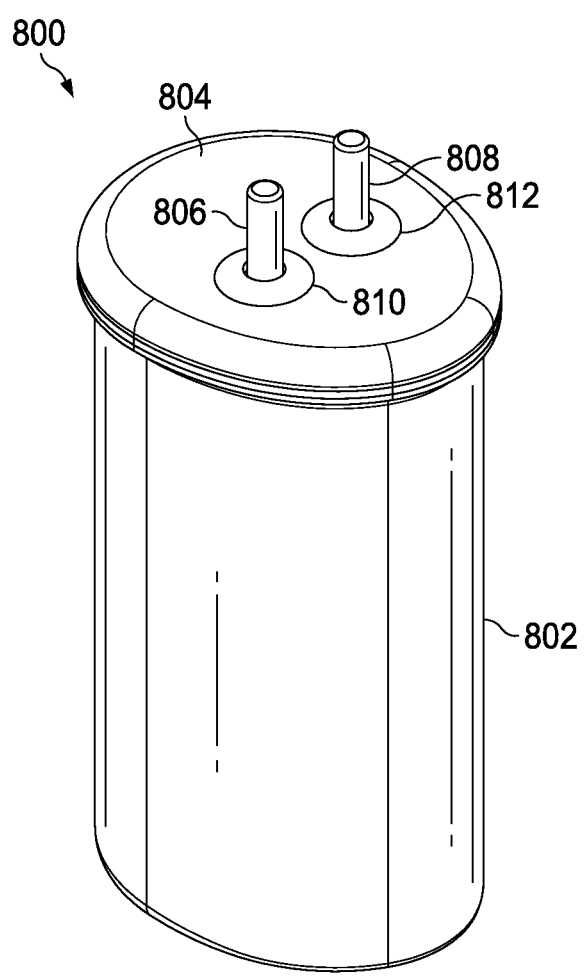
FIG. 8 is a perspective view illustrating additional details of another example embodiment of an installation regulator that may be associated with the therapy system of FIG. 1.

FIG. 8 is a perspective view of an installation regulator 800, illustrating details that may be associated with another example embodiment of the installation regulator 116. The installation regulator 800 generally includes a housing, which may be formed by a body 802 and a cap 804 coupled to the body 802, as shown in the example embodiment of FIG. 8. Some embodiments of the installation regulator 800 may have fluid ports adapted for coupling to a tube. For example, as shown in FIG. 8, the installation regulator 800 may have first fluid port such as the solution inlet port 806, which may extend through an inlet port opening 810 of the cap 804, and a second fluid port such as the solution outlet port 808, which may extend through an outlet port opening 812.

Figure 9A:
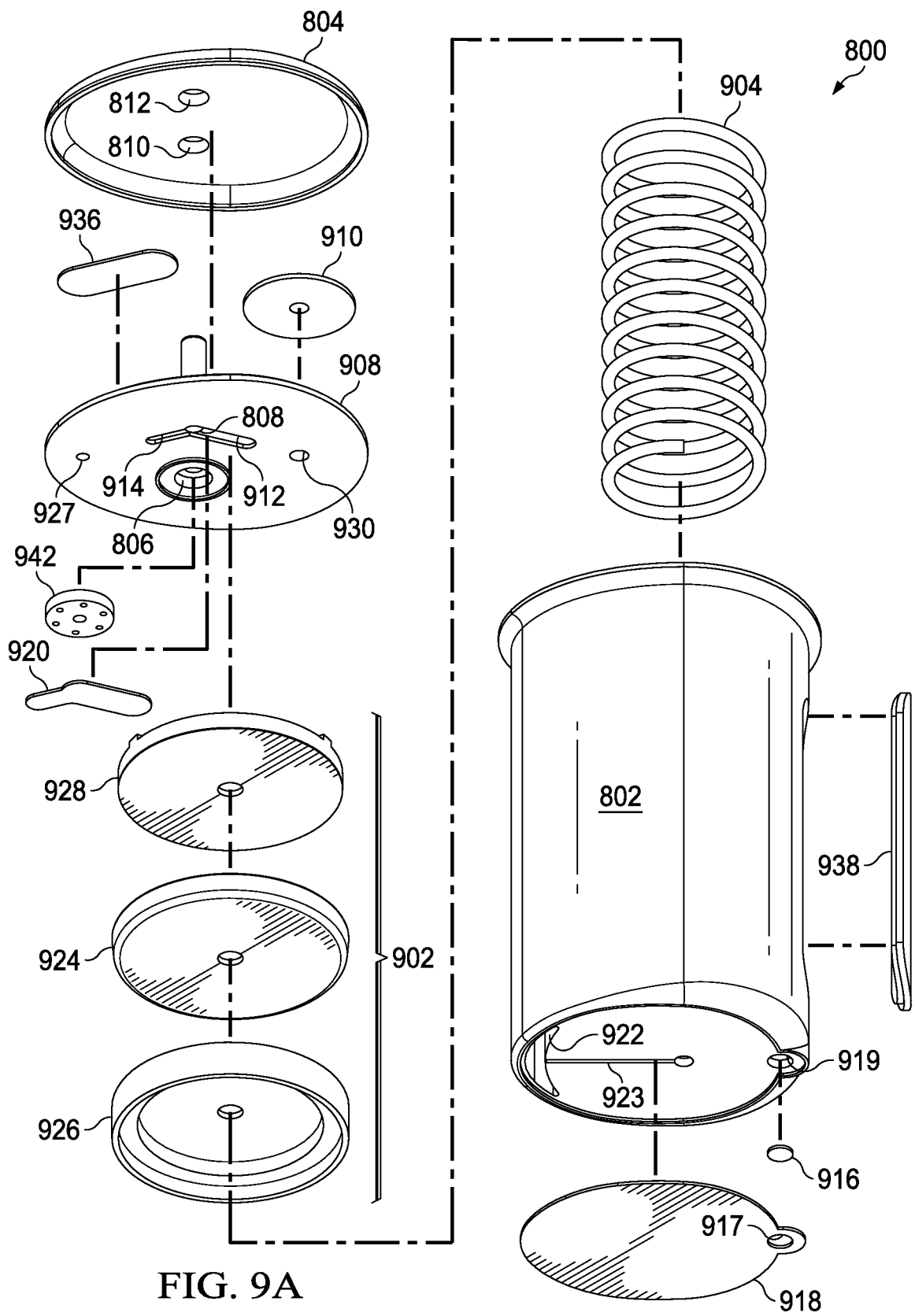
FIGS. 9A-9B are assembly views illustrating additional details that may be associated with some embodiments of the installation regulator of FIG. 8.
Figure 9B:
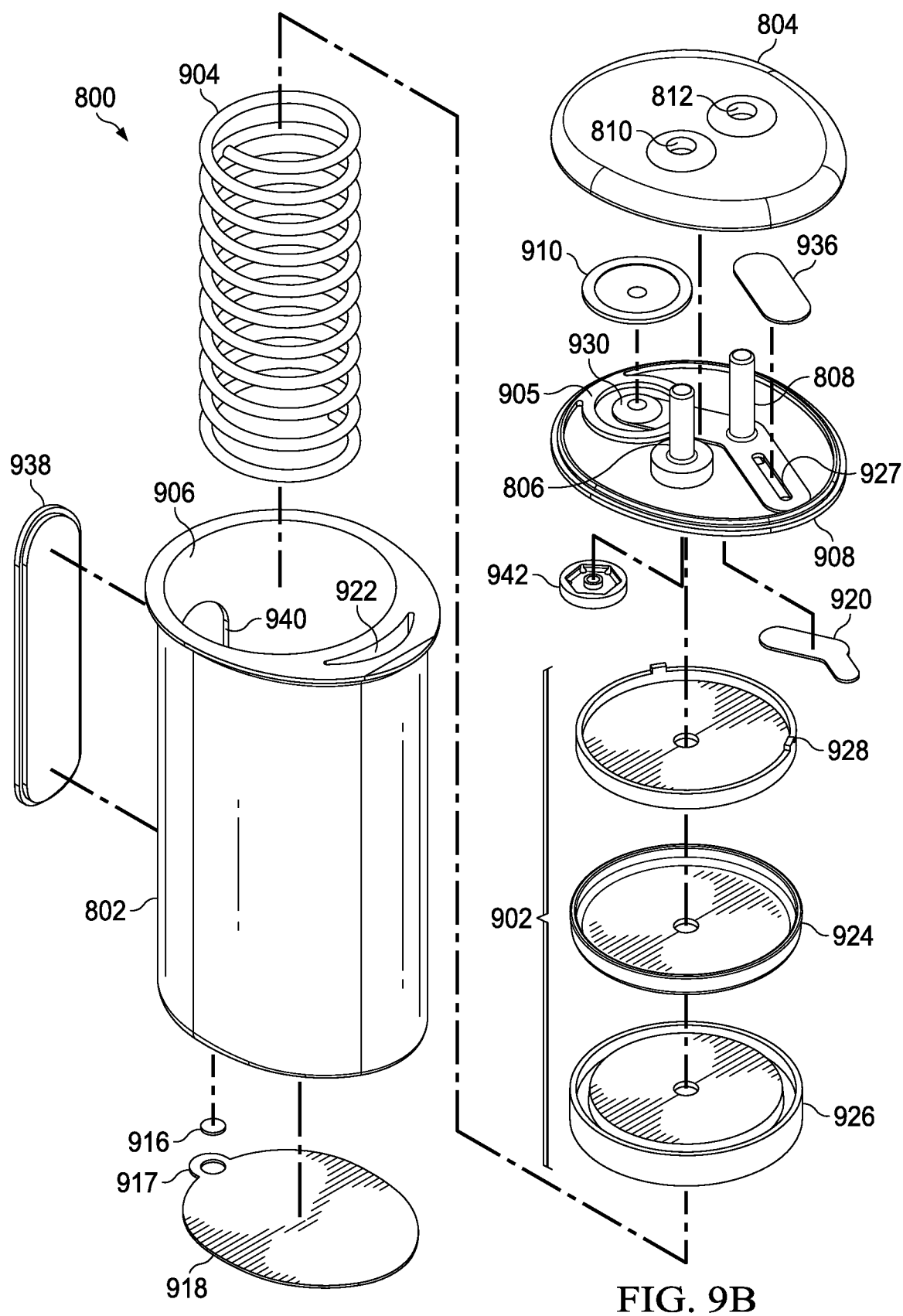

FIG. 9A and FIG. 9B are assembly views illustrating additional details that may be associated with some embodiments of an installation regulator, such as the installation regulator 800 of FIG. 8. Some embodiments of the installation regulator 800 may include a piston, an elastic device, and a gasket. The piston can be a flexible or movable barrier, for example, illustrated in FIG. 9A as a piston 902. An elastic device may be a spring or rubber, for example, illustrated in FIG. 9A as a spring 904. The spring 904 may be disposed within a cavity 906 of the body 802 of the installation regulator 800, generally between the piston 902 and the body 802, as illustrated in the example embodiment of FIG. 9B. In some embodiments, the spring 904 may be a coil spring coaxial with the piston 902, as shown in the example of FIG. 9A. Also as shown in the example embodiment of FIG. 9A and FIG. 9B, the cavity 906 may be a cylindrical bore, and the piston 902 may be rounded to fit within the cavity 906 of the body 802. The piston 902 may also reciprocate within the cavity 906.

The body 802 of the installation regulator 800 may also comprise a window 938, which may allow viewing the interior of the installation regulator 800 through an opening 940. For example, the position of the piston 902 or the fluid in the cavity 906 may be viewed through the window 938 and the opening 940 in some embodiments.

The instillation regulator 800 may also include a head 908, which may be disposed between the body 802 and the cap 804. The instillation regulator 800 may also include an outlet check valve 910 disposed between the head 908 and the cap 804. For example, the outlet check valve 910 may be a diaphragm valve comprising a flexible membrane or partition, such as a thin flexible disk. A membrane 936 may also be disposed between the cap 804 and a channel 927 of the head 908. The head 908 may comprise an extension 905, and a valve seat 930 within the extension 905 configured to engage the outlet check valve 910.

Some embodiments of the instillation regulator 800 may also include a flow limiter. For example, a flow limiter may comprise a hydrophobic filter 916, as illustrated in FIG. 9A and FIG. 9B. The hydrophobic filter 916 is generally configured to be disposed in or otherwise engage a vent 919, and retaining ring 917 may be disposed around or otherwise coupled to the hydrophobic filter 916 and the vent 919 to couple the hydrophobic filter 916 to the vent 919. The retaining ring 917 may be coupled to or integral with a sealing membrane 918, as illustrated in the example embodiment of FIG. 9A and FIG. 9B.

The head 908 may also include a passage configured to fluidly couple the valve seat 930 to the solution outlet port 808. For example, an integrated fluid conductor may be formed by a membrane 920 coupled to the head 908 to enclose a channel 912 formed in the head 908. Another passage may fluidly couple the solution outlet port 808 to the channel 927. For example, an integrated fluid conductor may be formed by coupling the membrane 920 to the head 908 to enclose a channel 914. The membrane 936 may also be coupled to the head 908 to enclose the channel 927. In some embodiments, any or all of the channel 912, the channel 914 and the channel 927 may be integrally molded into the head 908.

The body 802 may also include one or more passages configured to fluidly couple the channel 927 to the cavity 906. For example, the body 802 may include a fluid conductor formed by the sealing membrane 918 coupled to the body 802 to enclose a channel 923, and a passage 922 in the body 802 may fluidly couple the channel 923 and the channel 927. In some embodiments, either or both of the passage 922 and the channel 923 may be integrally molded in the body 802.

In some embodiments, the piston 902 may comprise a conformable seal disposed between a base and a retainer. For example, the piston 902 of FIG. 9A and FIG. 9B includes a seal 924, a seal base 926, and a seal retainer 928. The seal 924 may be an elastomer or other flexible material, for example, while the seal base 926 and the seal retainer 928 may be a rigid plastic to provide strength and rigidity to support the seal 924. An inlet check valve 942 may also be disposed between the head 908 and the seal retainer 928, fluidly coupled to the solution inlet port 806.

Figure 10:
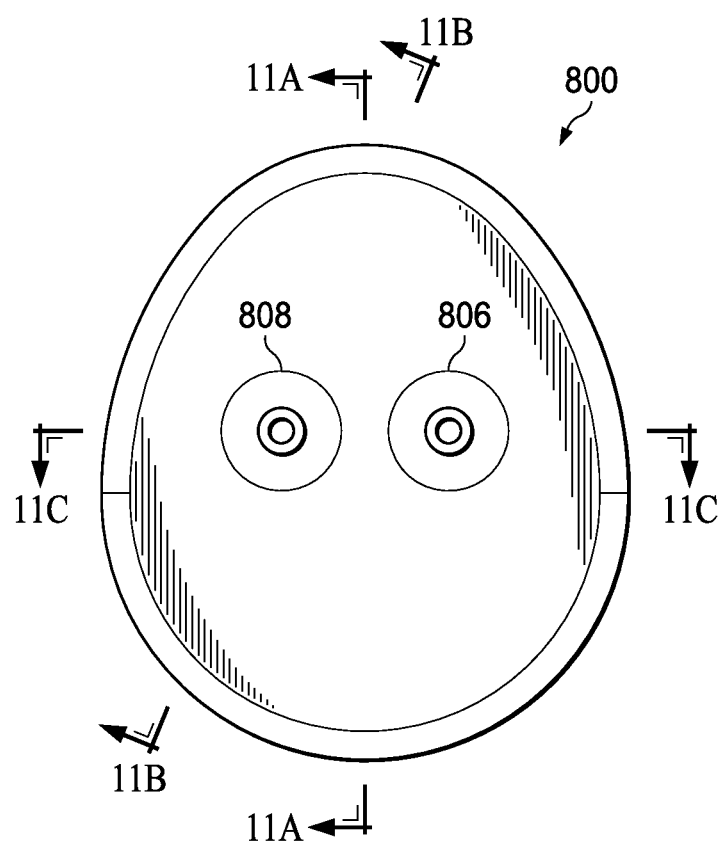
FIG. 10 is a top view illustrating additional details that may be associated with some embodiments of the installation regulator of FIG. 8.

FIG. 10 is a top view illustrating additional details that may be associated with some embodiments of an instillation regulator, such as the instillation regulator 800. As illustrated in the example embodiment of FIG. 10, the instillation regulator 800 may have an ovate profile to accommodate the cavity 906 and the passage 922.

Figure 11A:
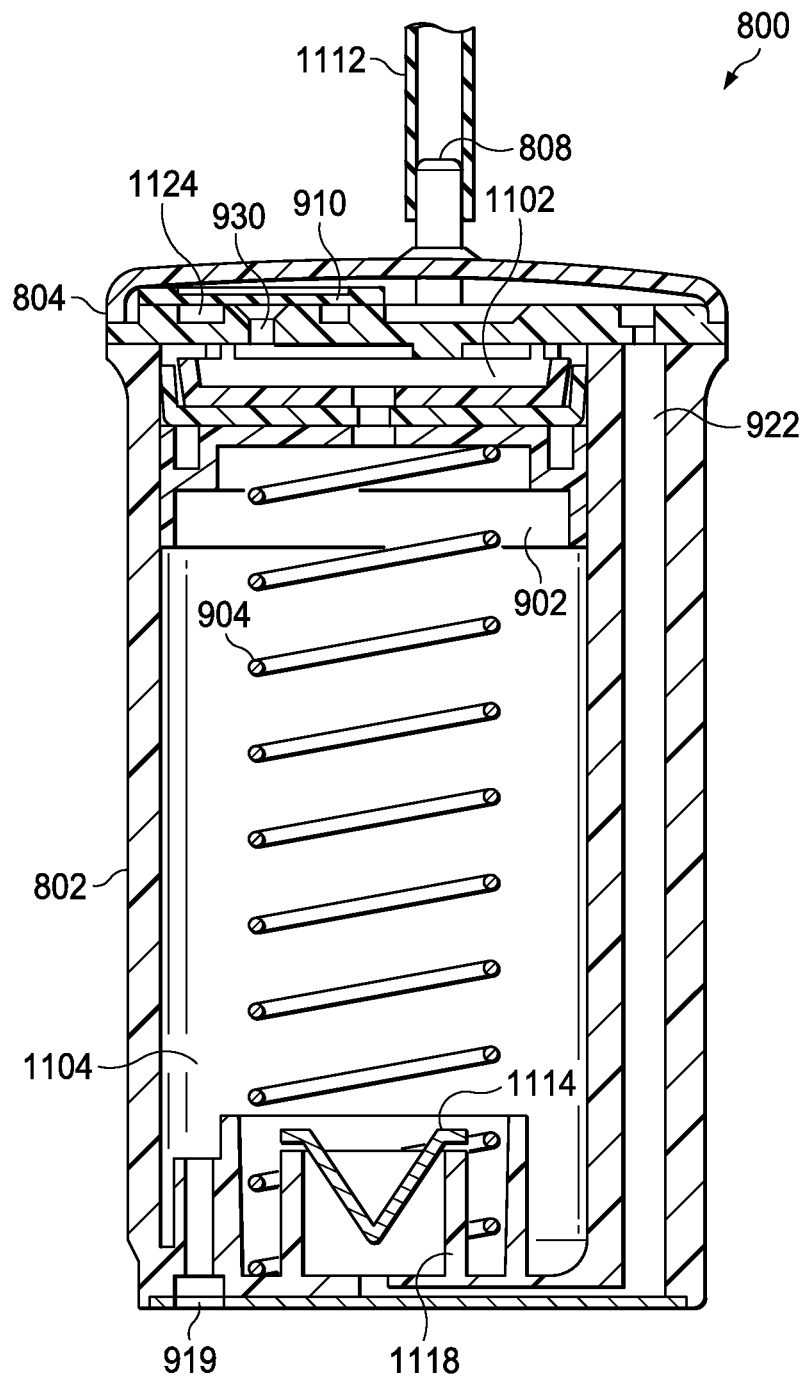
FIG. 11A is a cross-section of the installation regulator shown in FIG. 10 taken along line 11A-11A.
Figure 11B:
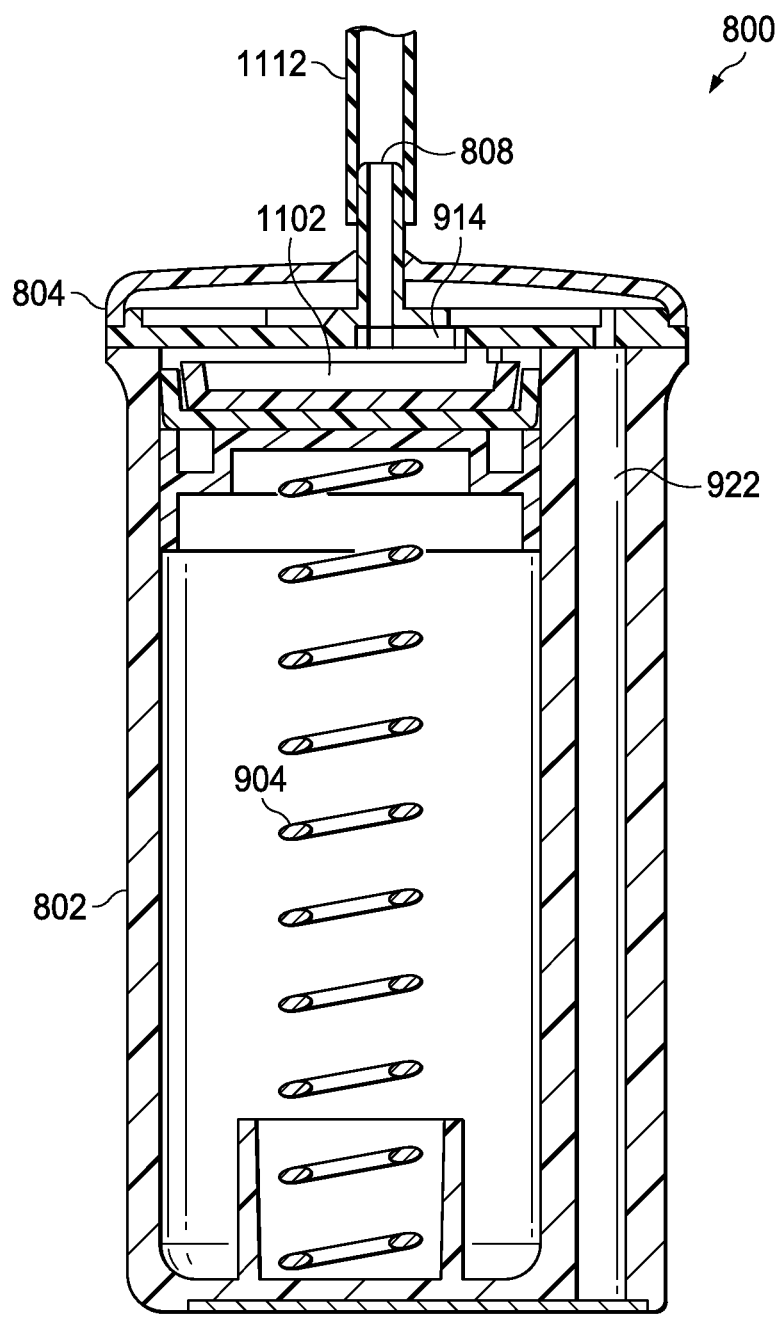
FIG. 11B is a cross-section of the installation regulator shown in FIG. 10 taken along line 11B-11B.
Figure 11C:
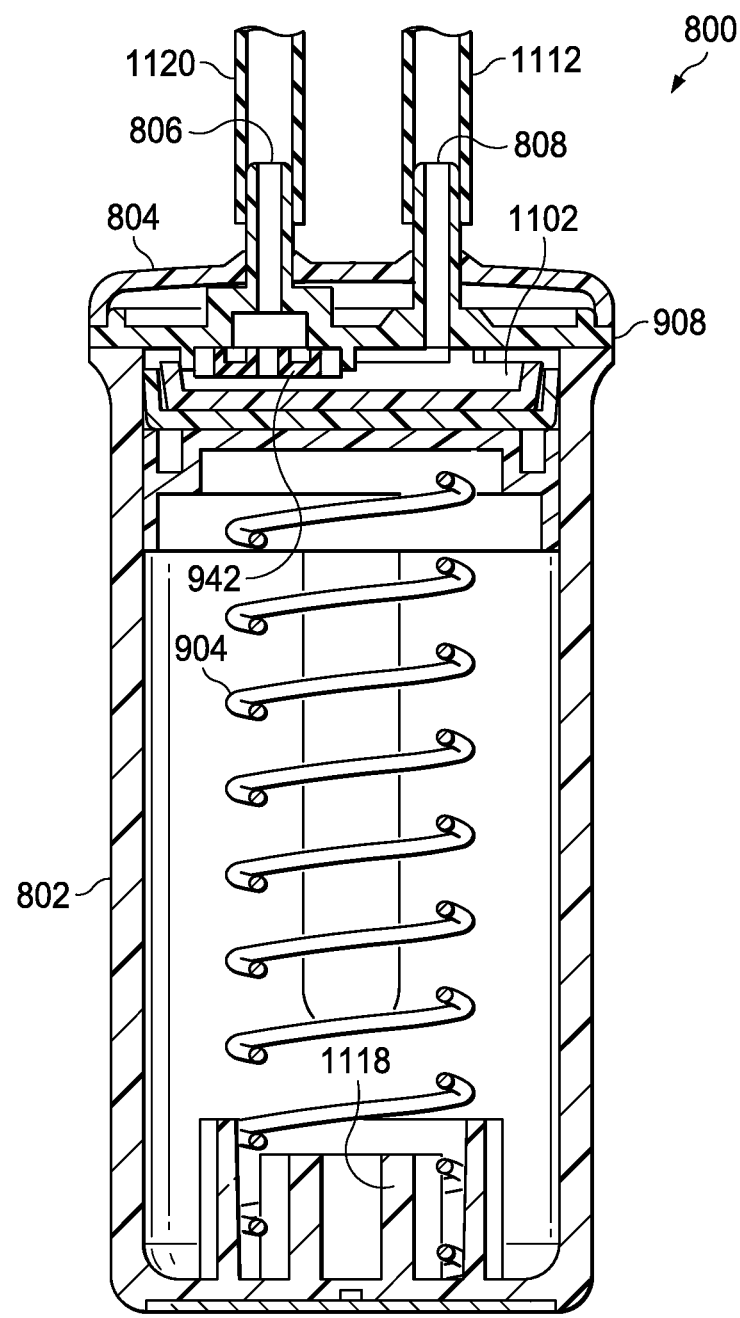
FIG. 11C is a cross-section of the installation regulator shown in FIG. 10 taken along line 11C-11C.

FIG. 11A is a sectional view of the instillation regulator 800 of FIG. 10 taken on line 11A-11A, illustrating additional details that may be associated with some embodiments of the instillation regulator 800. FIG. 11B is a sectional view of the instillation regulator 800 of FIG. 10 taken on line 11B-11B, illustrating additional details that may be associated with some embodiments of the instillation regulator 800. FIG. 11C is a sectional view of the instillation regulator 800 of FIG. 10 taken on line 11C-11C, illustrating additional details that may be associated with some embodiments of the instillation regulator 800. Assembled as shown in the example embodiment of FIG. 11A, the head 908 can be coupled to the body 802 to fluidly isolate the cavity 906 from the ambient environment, and the piston 902 may partition or separate the cavity 906 into a first chamber 1102 and a second chamber 1104. Moreover, the piston 902 may engage the body 202 to provide a seal between the first chamber 1102 and the second chamber 1104. For example, as shown in the example embodiment of FIG. 11A, the seal 924 may press against a side wall of the body 802 to fluidly isolate the first chamber 1102 from the second chamber 1104.

The outlet check valve 910 may be coupled to the extension 905 to form a third chamber 1124, generally defined by a portion of the head 908, the extension 905, and the outlet check valve 910. In some embodiments, a peripheral edge of the outlet check valve 910 may be supported or coupled to the extension 905. Additionally or alternatively, the cap 804 may be disposed on the head 908 to secure the outlet check valve 910 to the extension 905. A passage through the valve seat 930 may fluidly couple the first chamber 1102 and the third chamber 1124. The channel 912 may also fluidly couple the third chamber 1124 to the solution outlet port 808.

The inlet check valve 942 may be fluidly coupled to the first chamber 1102 and configured to be opened by negative pressure in the first chamber 1102. Some embodiments may also comprise an outlet check valve 910 fluidly coupled to the second chamber 1104 and configured to be opened by negative pressure in the channel 923 or by an increased pressure in the second chamber 1104. For example, the inlet check valve 942 may be disposed between the solution inlet port 806 and the first chamber 1102, and the outlet check valve 1114 may be disposed between the solution outlet port 808 and the second chamber 1104.

The spring 904 may be disposed between the piston 902 and the body 802 in some embodiments. For example, as shown in the illustrative embodiment of FIGS. 11A-11C, the spring 904 may have a first end disposed around a retention boss 1118 to restrict lateral movement, and may have a second end engaged to the piston 902.

In operation, the instillation regulator 800 may be primed during negative-pressure intervals, and may instill a solution during venting intervals. For example, during a negative-pressure interval, negative pressure can be supplied by a negative-pressure therapy unit (not shown) and delivered by a tube 1112 to the instillation regulator 800. In the embodiment of FIGS. 11A-11C, negative pressure may be delivered to the second chamber 1104 through the solution outlet port 808, the passage 922, and the channel 923. Negative pressure in the second chamber 1104 can move the piston 902, expanding the first chamber 1102 and compressing the second chamber 1104. If the first chamber 1102 expands, pressure in the first chamber 1102 can decrease proportionately. Negative pressure in the first chamber 1102 can have the effect of actively drawing instillation solution into the first chamber 1102 through the solution inlet port 806. The distance that the piston 902 travels can determine a dosage volume of instillation solution. The first chamber 1102 may be lined with a suitable material to prevent contamination from mechanical components or lubricants. For example, the first chamber 1102 may be lined with a film bag, an elastomeric bag, or a compressible bellows.

In some embodiments, the installation dosage may be adjusted. Such capability may be achieved by adjusting the distance traveled of the movable components during negative-pressure and venting intervals. For example, the spring 904 may be compressed so that the distance traveled by the piston 902 will be limited. This may result from more quickly reaching the point where the negative pressure applied to the second chamber 1104 for compressing the spring 904 can no longer overcome the force exerted by the spring 904. Other example embodiments may adjust the installation dosage by reducing the height of the second chamber 1104, for example, by screwing the first chamber 1102 further into the second chamber 1104 using a threaded mechanism. Yet another example may include controlling the dosage of instillation fluid delivered by limiting the travel of the piston 902 within the second chamber 1104 by adjusting the height of a stop block located within the second chamber 1104, under the piston 902. Additional examples may include restricting the flow of instillation fluid through either the solution inflow tube 1120 or the solution outflow tube 1112 using, for example, a valve, or by restricting the rate at which the piston 902 recovers.

Expansion of the first chamber 1102 may also have the effect of decreasing pressure in the third chamber 1124, as pressure between the first chamber 1102 and the third chamber 1124 may be equalized through the passage 1126. The decreased pressure in the third chamber 1124 may have the effect of closing the outlet check valve 910, which can prevent instillation of solution to a dressing during a negative-pressure interval.

During a venting interval, the vent 919 may provide fluid communication between the second chamber 1104 and the ambient environment, which can also have the effect of increasing pressure in the second chamber 1104. Increased pressure in the second chamber 1104 during a venting interval can have the effect of moving the piston 902, compressing the first chamber 1102 and expanding the second chamber 1104. If the first chamber 1102 is compressed, pressure in the first chamber 1102 can increase proportionately. The resulting increase in pressure can move solution out of the first chamber 1102 through the valve seat 930, the channel 912, and the solution outlet port 808, instilling solution to a tissue site through the solution outflow tube 1112. The inlet check valve 942 can prevent back-flow through the solution inlet port 806 during instillation, and the outlet check valve 1114 can prevent solution from moving into the second chamber 1104 from the channel 923 during instillation. A flow limiter such as the hydrophobic filter 916 can control the rate of venting between the second chamber 1104 and the ambient environment through the vent 919, which can also determine the rate at which the piston 902 moves and the rate at which solution can be instilled from the first chamber 1102. For example, the surface area of the hydrophobic filter 916 can determine the vent rate and can be calibrated to provide a prescribed instillation rate.

The systems, apparatuses, and methods described herein may provide significant advantages. For example, an instillation regulator described above can combine instillation therapy with negative-pressure therapy without an additional pump. The use of a single pump, rather than two separate pumps, may provide a more compact, lighter, and less expensive therapy system. Furthermore, embodiments of the instillation regulator described above may be incorporated into therapy systems without making changes to existing negative-pressure therapy devices that use intermittent therapy. Additionally, the use of an instillation regulator such as described herein may offer a way to ensure that reliable and repeatable dosages of instillation fluid are delivered to a tissue site. Dosage amounts may also be easily adjusted through the use of an instillation regulator. The instillation regulator embodiments described above may also provide an ability to better deal with head heights when instilling fluid, as compared to other non-powered or powered delivery systems.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An instillation regulator, comprising:
   a first chamber;
   an inlet check valve fluidly coupled to the first chamber;
   a first outlet check valve fluidly coupled to the first chamber;
   a second chamber;
   a second outlet check valve fluidly coupled to the second chamber;
   a flow limiter fluidly coupled to the second chamber;
   a piston separating the first chamber and the second chamber; and
   a spring disposed against the piston in the second chamber to bias the piston.

2. The instillation regulator of claim 1, wherein the first chamber, the second chamber, the first outlet check valve, the second outlet check valve, the piston, and the spring are disposed within a housing, the housing comprised of a body and a head coupled to the body.

3. The instillation regulator of claim 1, wherein the first outlet check valve is fluidly coupled to the second outlet check valve.

4. The instillation regulator of claim 1, wherein the first outlet check valve is a diaphragm valve configured to be closed by negative pressure in the first chamber.

5. The instillation regulator of claim 1, wherein the inlet check valve is configured to be opened by negative pressure in the first chamber.

6. The instillation regulator of claim 1, wherein the piston is configured to be displaced by a pressure differential between the first chamber and the second chamber.

7. The instillation regulator of claim 1, wherein the flow limiter is a needle valve.

8. The instillation regulator of claim 1, wherein the flow limiter comprises a hydrophobic filter and a vent fluidly coupling the hydrophobic filter to the second chamber.

9. The instillation regulator of claim 1, wherein the piston comprises a seal disposed between a base and a retainer.

10. The instillation regulator of claim 1, further comprising:
a negative-pressure port fluidly coupled to the second outlet check valve;
wherein the second outlet check valve is fluidly coupled to the second chamber and configured to be opened by negative pressure delivered to the negative-pressure port.

11. The instillation regulator of claim 1, further comprising:
an inlet port fluidly coupled to the inlet check valve and the first chamber; and
an outlet port fluidly coupled to the first outlet check valve.

12. The instillation regulator of claim 1, further comprising:
a body;
a head coupled to the body to enclose the piston;
an outlet port; and
a channel through the body fluidly coupling the outlet port to the second chamber.

13. A system for treating a tissue site, comprising:
a dressing for placing on the tissue site;
a negative-pressure source fluidly coupled to the dressing, the negative-pressure source configured for a negative-pressure interval and a venting interval;
a solution source; and
an instillation regulator fluidly coupled to the solution source and to the dressing, the instillation regulator configured to draw a solution from the solution source during the negative-pressure interval and to instill the solution to the dressing during the venting interval;
wherein the instillation regulator comprises:
a housing comprising a cavity, and
a piston partitioning the cavity into a first chamber and a second chamber.

14. The system of claim 13, wherein the instillation regulator further comprises:
an inlet check valve fluidly coupled to the first chamber;
a first outlet check valve fluidly coupled to the first chamber; and
a second outlet check valve fluidly coupled to the second chamber.

15. The system of claim 13, further comprising a pressure regulator fluidly coupled to the negative-pressure source and the dressing.

16. The system of claim 13, further comprising a container fluidly coupled to the negative-pressure source and the dressing and configured to collect fluids.

17. The system of claim 13, further comprising a connection interface configured to fluidly connect the instillation regulator and the negative-pressure source to the dressing.

18. The system of claim 17, wherein the connection interface is a multi-port elbow connector.

19. The system of claim 13, wherein the dressing comprises:
a tissue interface adapted to be placed proximate to the tissue site; and
a cover adapted to be placed over the tissue interface.

20. A method for treating a tissue site, the method comprising:
applying a dressing to the tissue site;
coupling a negative-pressure source to the dressing, the negative-pressure source configured to provide a negative-pressure interval and a venting interval;
coupling an instillation regulator to the dressing;
coupling a solution source to the instillation regulator;
drawing a solution to the instillation regulator from the solution source during the negative-pressure interval; and
instilling the solution from the instillation regulator to the dressing during a venting interval;
wherein the instillation regulator comprises:
a first chamber,
a second chamber, and
a piston separating the first chamber and the second chamber.

21. The method of treatment of claim 20, wherein the instillation regulator further comprises:
an inlet check valve fluidly coupled to the first chamber;
a first outlet check valve fluidly coupled to the first chamber;
a second outlet check valve fluidly coupled to the second chamber; and
a spring in the second chamber between the piston and the second outlet check valve.

22. The method of treatment of claim 21, wherein the instillation regulator further comprises:
a body; and
a channel formed in and extending a length of the body to provide a fluid path for negative pressure to be delivered to the second outlet check valve.

23. An apparatus for instilling a solution to a tissue site, the apparatus comprising:
a body comprising a negative-pressure port, a vent, and a cavity;
a head coupled to the body and having an extension, a solution inlet port, and a solution outlet port;
a piston disposed in the cavity and partitioning the cavity into a first chamber and a second chamber;
a spring disposed within the second chamber between the piston and the body;
a first outlet check valve fluidly coupled to the extension between the first chamber and the solution outlet port, wherein the first outlet check valve is configured to be closed by negative pressure in the first chamber;
a hydrophobic filter disposed in the vent;
retaining ring coupled to the hydrophobic filter and the vent;
an inlet check valve fluidly coupled to the first chamber and configured to be opened by negative pressure in the first chamber; and
a second outlet check valve fluidly coupled to the second chamber and configured to be opened by negative pressure delivered to the negative-pressure port.

24. The apparatus of claim 23, further comprising:
a dressing fluidly coupled to the solution outlet port and to the negative pressure port;
a negative-pressure source fluidly coupled to the dressing, the negative-pressure source configured for a negative-pressure interval and a venting interval; and
a solution source fluidly coupled to the solution inlet port.

25. An apparatus for instilling a solution to a tissue site, the apparatus comprising:
a body comprising a vent and a cavity;
a head coupled to the body and comprising an extension, a first fluid port, and a second fluid port;
a piston disposed in the cavity and partitioning the cavity into a first chamber and a second chamber;
a spring disposed within the second chamber between the piston and the body;

a first channel integrally molded in the head;

a second channel integrally molded in the body and fluidly coupled to the second chamber;

a passage integrally molded along a length of the body, the passage fluidly coupled to the first channel and to the second channel;

a first outlet check valve fluidly coupled to the extension between the first chamber and the second fluid port, wherein the first outlet check valve is configured to be closed by negative pressure in the first chamber;

an inlet check valve fluidly coupled to the first chamber and configured to be opened by negative pressure in the first chamber; and a second outlet check valve fluidly coupled to the second chamber and configured to be opened by negative pressure in the second channel.

26. The apparatus of claim 25, further comprising:

a dressing fluidly coupled to the second fluid port;

a negative-pressure source fluidly coupled to the dressing, the negative-pressure source configured for a negative-pressure interval and a venting interval; and a solution source fluidly coupled to the first fluid port.

* * * * *